(12) United States Patent
Rynhart et al.

(10) Patent No.: US 6,553,813 B2
(45) Date of Patent: *Apr. 29, 2003

(54) MOISTURE METER WITH IMPEDANCE AND RELATIVE HUMIDITY MEASUREMENTS

(75) Inventors: Alan Rynhart, Wicklow (IE); John Fallon, Dublin (IE); James McIlroy, Dublin (IE)

(73) Assignee: Rynhart Research Limited, Delgany (IE)

( * ) Notice: Subject to any disclaimer, the term of this patent is extended or adjusted under 35 U.S.C. 154(b) by 19 days.

This patent is subject to a terminal disclaimer.

(21) Appl. No.: 09/794,007

(22) Filed: Feb. 28, 2001

(65) Prior Publication Data

US 2001/0017053 A1 Aug. 30, 2001

(30) Foreign Application Priority Data

Feb. 29, 2000 (IE) .......................................... 2000/0158

(51) Int. Cl.⁷ .......................... G01N 25/26; G01N 5/02; G01R 27/32
(52) U.S. Cl. .............................. 73/73; 73/74; 324/640; 324/664
(58) Field of Search ........................... 73/73, 74, 866.5, 73/431, 29.01

(56) References Cited

U.S. PATENT DOCUMENTS

| | | | |
|---|---|---|---|
| 5,382,908 A | | 1/1995 | Forsström et al. ............ 324/439 |
| 5,396,796 A | * | 3/1995 | Kotani et al. ..................... 73/431 |
| 5,493,229 A | | 2/1996 | McMahon .................... 324/664 |
| 5,621,669 A | * | 4/1997 | Bjornsson .................. 364/571.01 |
| 6,276,202 B1 | * | 8/2001 | Latarius ...................... 73/335.05 |
| 6,340,892 B1 | * | 1/2002 | Rynhart et al. ............... 324/640 |

FOREIGN PATENT DOCUMENTS

| | | |
|---|---|---|
| CH | 663472 A5 | 12/1987 |
| EP | 0074780 A2 | 3/1983 |
| JP | 11-6797 | 1/1999 |
| WO | WO92/07251 | 4/1992 |

* cited by examiner

*Primary Examiner*—Daniel S. Larkin
*Assistant Examiner*—Rodney Frank
(74) *Attorney, Agent, or Firm*—Jacobson Holman PLLC

(57) ABSTRACT

A moisture meter (1) has a hand-held casing (2) with a digital microcontroller (50), LCD display (4), and a keypad (3). Spring-loaded contacts (6) contact material and allow capacitive impedance measurement via electrodes (5) and drive/pickup circuits (20). Also, a relative humidity probe (9) provides an input so that the processor generates both moisture contact near-surface measurements and also relative humidity measurements. This allows optimum analysis of material.

17 Claims, 13 Drawing Sheets

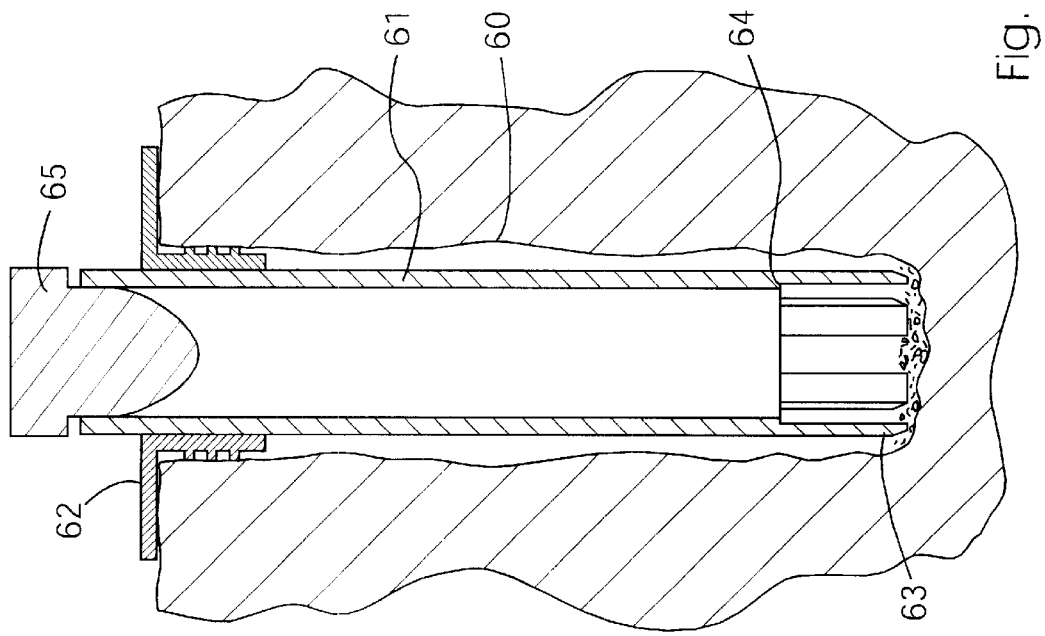
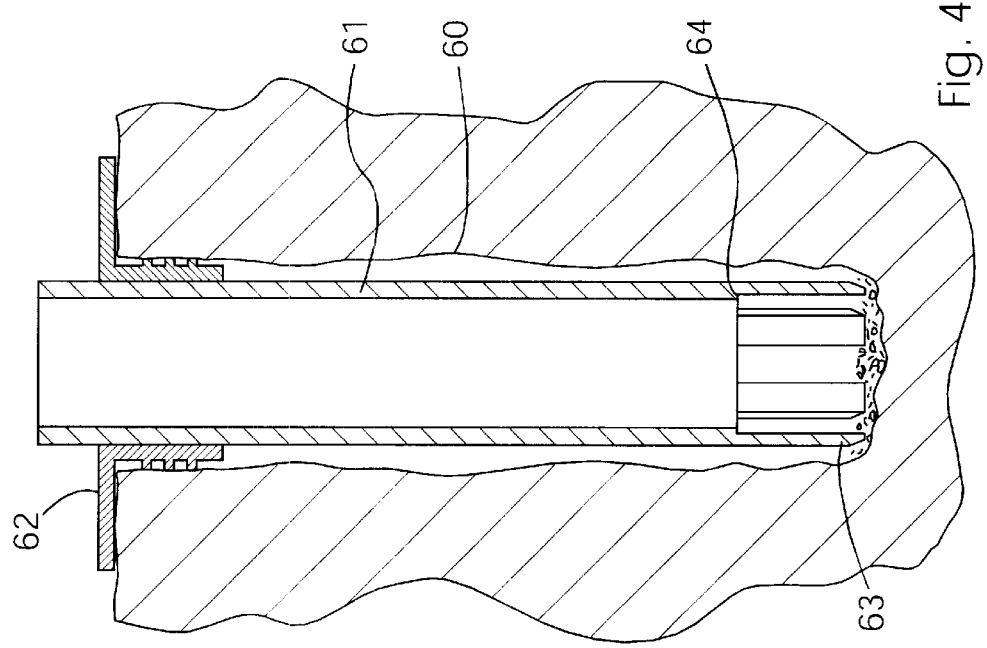
Fig. 4(a)
Fig. 4(b)

MOISTURE METER WITH IMPEDANCE AND RELATIVE HUMIDITY MEASUREMENTS

FIELD OF THE INVENTION

The invention relates to a moisture meter, particularly for masonry materials such as concrete or gypsum structures.

PRIOR ART DISCUSSION

Concrete floors must be allowed to dry to an adequate level before they are covered with sheet, tiles, coatings or timber flooring. Excess moisture could lead to problems of condensation causing swelling and peeling of the covering and condensation, blistering or deterioration of adhesives leading to flooring failure.

No period can be specified for the drying of concrete as this is affected by temperature and humidity within the building. For this reason the concrete slab should be regularly checked to monitor the drying process.

Japanese Patent Specification No. JP11006797 describes measurement of moisture content of cast concrete. The system uses infra-red radiation at a multiplicity of locations in a grid.

The invention is directed towards providing a moisture meter which allows simpler determination of masonry moisture content with excellent accuracy.

SUMMARY OF THE INVENTION

According to the invention, there is provided a moisture meter comprising:
 a hand-held housing;
 a controller;
 an input interface;
 an output interface;
 an electrical impedance sensor connected to the controller;
 a relative humidity probe connected to the controller;
 means in the controller for processing signals from the impedance sensor to generate a moisture content output, and for processing signals from the relative humidity probe to generate a relative humidity output.

In one embodiment, the controller comprises means for storing material parameter datasets for each of a plurality of materials, means for allowing user selection of a relevant dataset, and means for processing input signals according to the selected dataset.

In another embodiment, the controller comprises means for storing a dataset for each of concrete and gypsum.

In a further embodiment, the controller comprises means for storing a dataset for each of a plurality of concrete and gypsum types.

In a further embodiment, the relative humidity probe further comprises a temperature sensor and the controller comprises means for processing input signals from said sensor and for generating a temperature output.

In one embodiment, the impedance sensor comprises capacitive electrodes and associated drive and pick-up circuits.

Preferably, each electrode comprises a plurality of spring-loaded contacts for uniform contact with material.

In one embodiment, the drive frequency is approximately 125 kHz.

In another embodiment, the controller comprises means for storing a data record for each measurement of the impedance sensor and of the relative humidity probe.

In a further embodiment, the relative humidity probe further comprises a temperature sensor and the controller comprises means for writing temperature data to a relative humidity data record.

In one embodiment, the relative humidity probe comprises a capacitive sensor, a pulse width modulator for modulating output of the capacitive sensor and an averaging filter for averaging the modulated signal.

In one embodiment, the probe further comprises a digital microcontroller connected to receive an output from the averaging filter via an analog to digital converter.

In a further embodiment, the probe comprises a housing of tubular shape comprising openings at an inner end for access by air to internal sensing components.

Preferably, the probe housing is of castellated shape at its inner end.

In one embodiment, the probe further comprises a grommet comprising means for sealing around the probe at the mouth of a bore.

In another embodiment, the probe further comprises a sleeve comprising means for receiving the probe body when inserted in a bore.

In one embodiment, the sleeve is a friction fit within the grommet as describe above.

According to another aspect, the invention provides a moisture meter comprising:
 a hand-held housing;
 a controller;
 an input interface;
 an output interface;
 a relative humidity probe connected to the controller;
 means in the controller for processing signals from the relative humidity probe to generate a relative humidity output; and wherein
 said relative humidity probe comprises:
  a tubular housing containing sensing components, said housing having openings at an inner end thereof,
  a sleeve comprising means for receiving the probe housing and having openings at an inner end thereof,
  a grommet within which the sleeve is a friction fit, said grommet comprising means for engaging the rim of a bore to seal an annular gap around the sleeve when inserted in a bore, and
  a plug comprising means for sealing an outer opening of said sleeve to create a confined sensing space within the sleeve before insertion of the probe housing.

DETAILED DESCRIPTION OF THE INVENTION

BRIEF DESCRIPTION OF THE DRAWINGS

The invention will be more clearly understood from the following description of some embodiments thereof, given by way of example only with reference to the accompanying drawings in which:

FIGS. 4(a) to 4(d) are a sequence of diagrams illustrating setup and operation of the meter to capture data from a concrete slab;

DESCRIPTION OF THE EMBODIMENT

Figure 1:
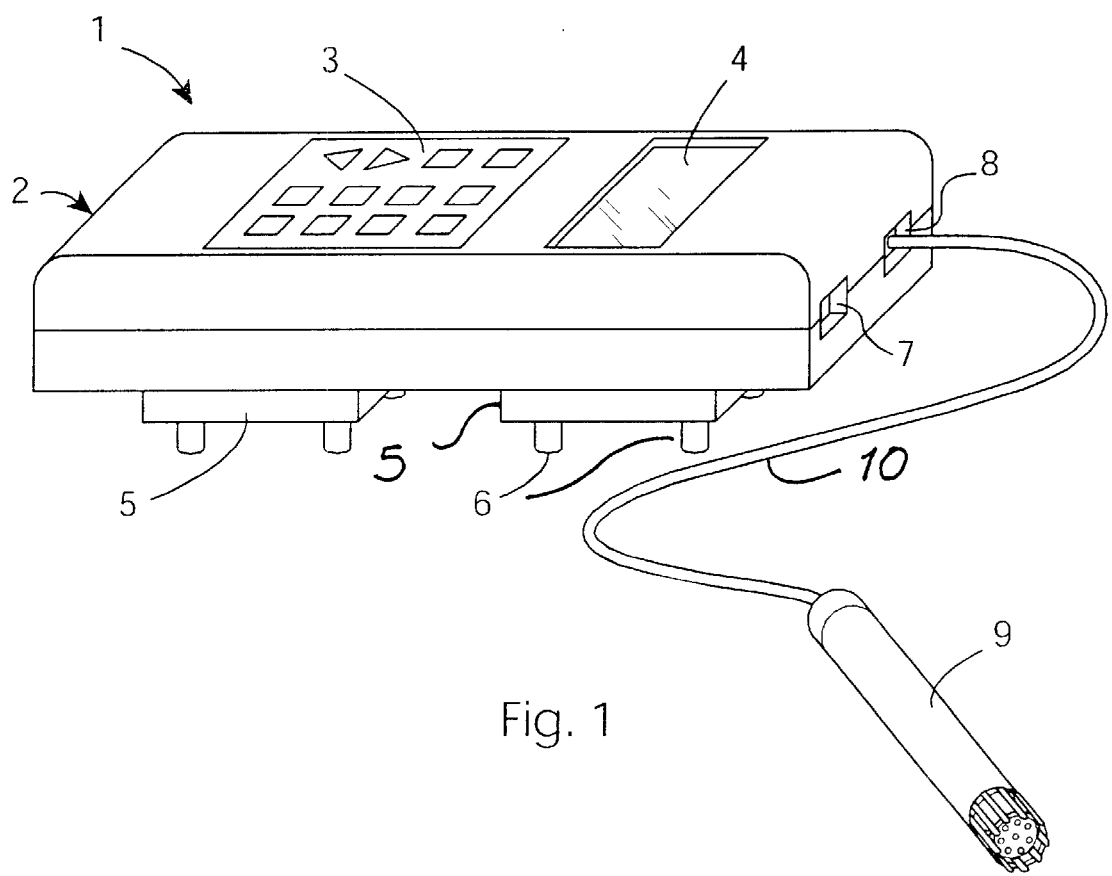
FIG. 1 is a perspective view from above of a moisture meter of the invention.

Referring to FIG. 1, a moisture meter 1 of the invention is shown. The meter 1 comprises a housing 2 supporting sensor and data processing circuits, a keypad 3, and a dot matrix display 4. The housing 2 also supports two electrodes 5 for impedance measurement and four spring-loaded gold-plated contacts 6 extending from each electrode 5. The contacts 6 each have a 4 mm plunger and a spring resistance of 300 grams. The meter 1 also comprises an RS232 socket 7 for connection to a computer, and a socket 8 connected by a lead 10 to a relative humidity probe 9. An on/off switch may also be connected in the top of the meter, alongside the socket 7.

Figure 2:
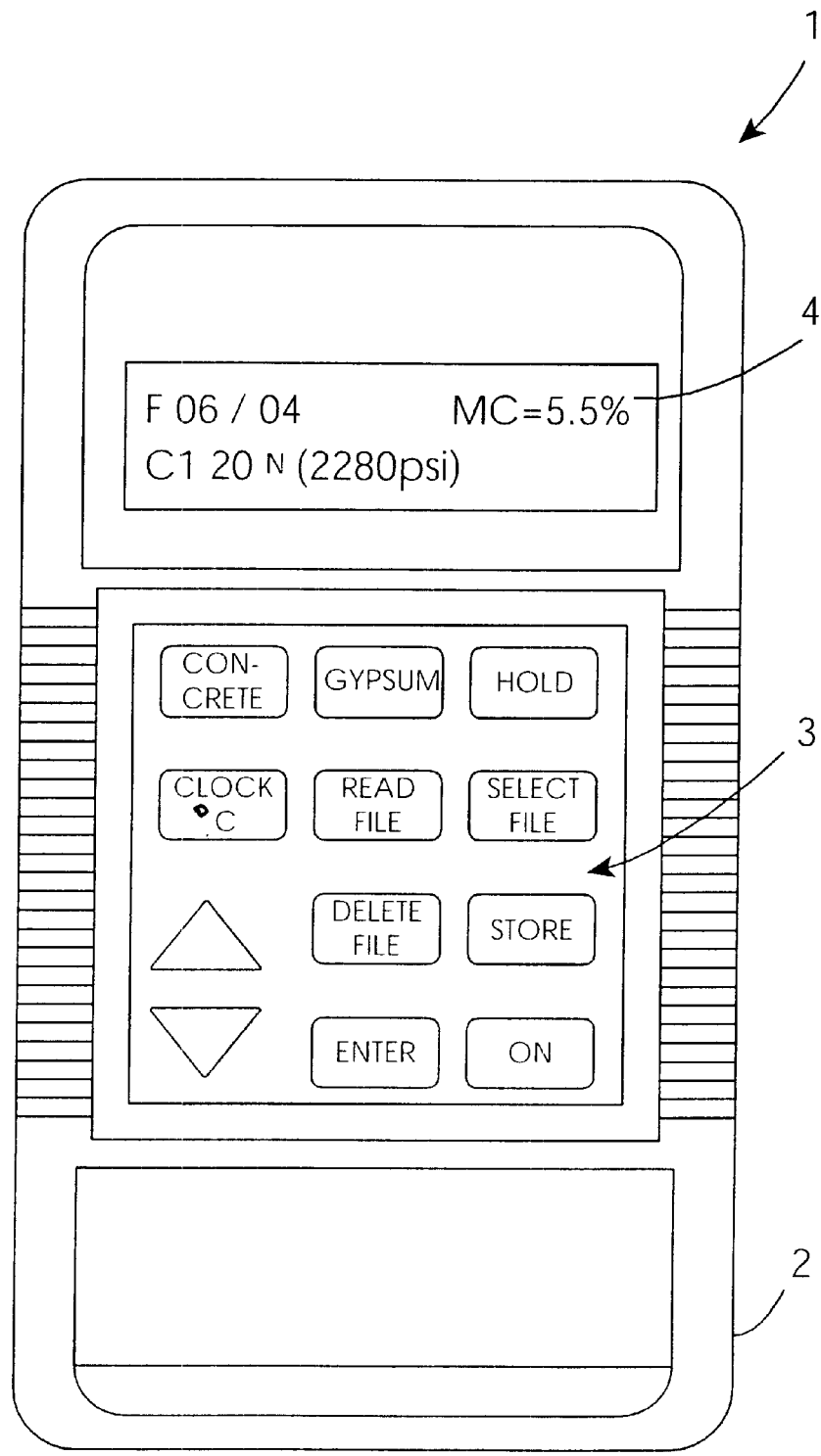
FIG. 2 is a front view of the moisture meter.

The keypad 3 is shown more clearly in FIG. 2. It comprises dedicated function keys for concrete and for gypsum selection. For data file management, there are Read File, Select File, Delete File, Store, and Enter keys. A further key (Clock/° C.) is used for adjustment and display of temperature and time data. There are also Hold and On keys, and arrow-shaped scroll keys.

The meter 1 allows measurement of the moisture content in four types of concrete and four types of gypsum. The basis of the measurement is capacitive measurement using the electrodes 5 and contacts 6 and relative humidity measurement using the probe 9.

The data processing is performed by a main microcontroller within the housing 2 and having an in-built A/D converter and RS 232/I$^2$C facilities. The microcontroller is connected to a non-volatile memory for storing readings, a materials library of parameter values, and settings. The materials library in this embodiment includes four concrete types and four gypsum types, however, this may vary according to requirements. Readings are stored in records, there being one record per reading, twenty five records per file, and a total of twenty five files. The circuits include a temperature sensor and a real-time clock, the latter of which has an independent battery backup.

The meter 1 can connect to a personal computer (PC) serial port via a cable plugged into the RS232 port 7. An associated PC application provides the following facilities:

1. Bi-directional RS232 serial communication to the instrument.
2. Download and view of the stored readings.
3. Ability to add notes to files and individual readings.
4. Ability to transfer downloaded data to a spreadsheet such as Microsoft Excel™ for analysis, graphical presentation, etc.
5. Ability to print downloaded data or library.

The microcontroller has the following features:
4 Kilobyte program memory.
8 bit analogue to digital converter preceded by an 8 channel analogue multiplexer.
2 wire serial communications (I$^2$C) module.
Serial communications interface (RS232) module.
33 input/output ports.

The non-volatile memory comprises a serial electrically erasable PROM. This IC is an 8 pin DIL package and read/write is via the I$^2$C two wire serial bus. The memory capacity is 64 Kilobits (8 Kbytes) which is divided into a 4 Kbit high endurance block with a 1 million (typical) erase/write capability and a 60 Kbit array with a 10,000 (typical) erase/write capability. The high endurance block is intended for frequently changed data such as instrument settings. The memory has an input cache for fast write loads with a capacity of 64 bits.

A serial real time clock IC is used. This device has the following features:

Counts seconds, minutes, hours, date of the month, month, day of the week, and year with leap year compensation valid up to the year 2100.
2-wire serial interface I$^2$C.
56 byte non-volatile RAM for data storage.
Automatic power fail detect and switch circuitry.
Consumes less than 500 nA in battery back-up mode.
8 pin DIL: package.

The real time clock requires two external components, a 32 kHz crystal and a small 3 volt lithium button type back-up cell to ensure that the time is maintained during main battery failure/replacement.

A serial digital temperature IC is used to measure the ambient temperature within the instrument. This is also an 8 pin DIL: package and operates on the 2 wire serial I$^2$C bus. Temperature accuracy is +/−0.5° C.

A RS232 interface circuit translates the serial communications interface levels of 0 to +5 volts to the PC voltage range. A discrete transistor arrangement is used for the RS232 interface circuit.

Figure 3:
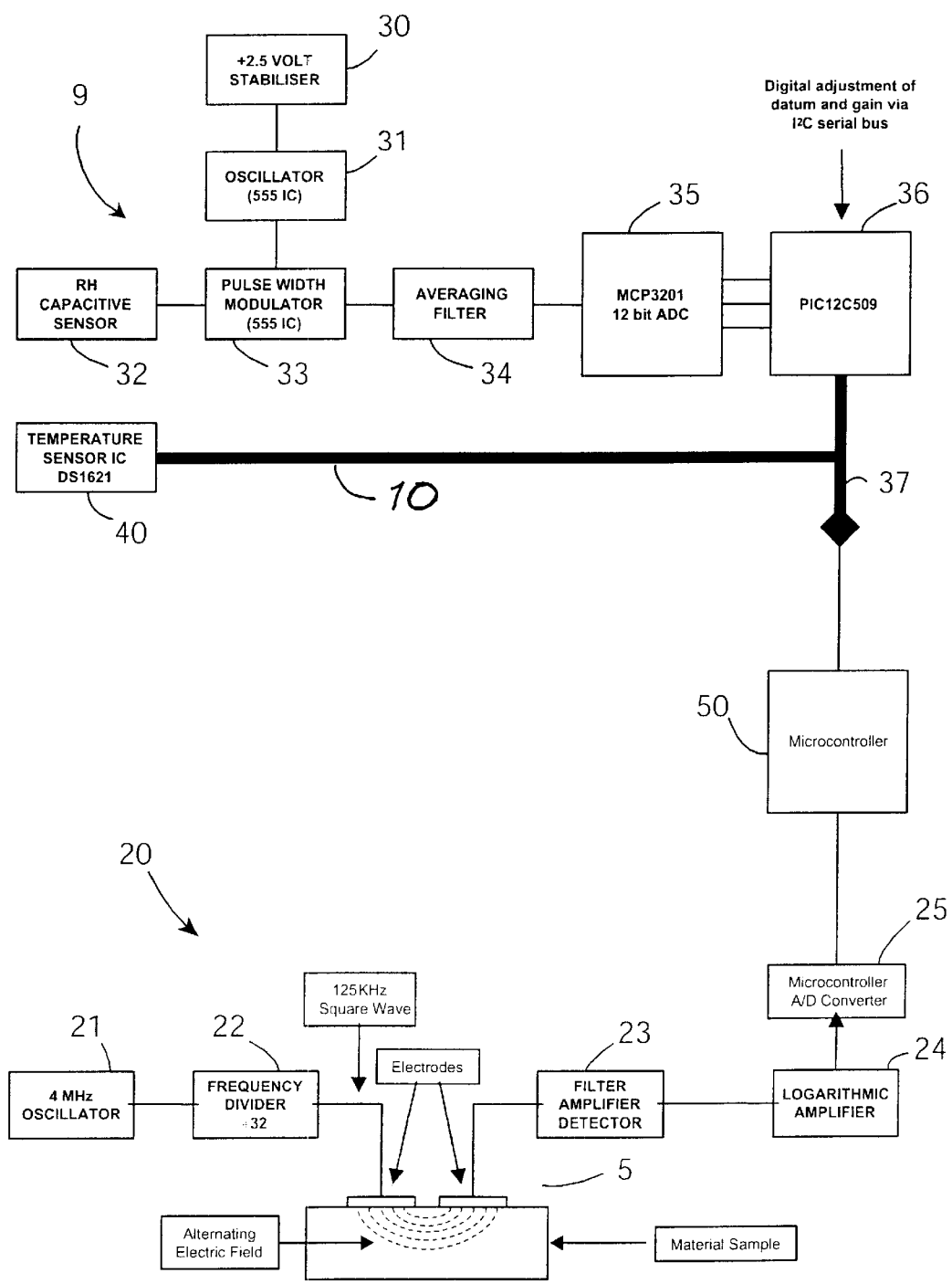
FIG. 3 is a diagram illustrating sensors of the meter.

Referring to FIG. 3, the probe 9 and the capacitive transducer (indicated generally by the number 20) are illustrated. The electrodes 5 contact the material in a uniform manner because of the four spring-loaded and gold-plated contacts 6 on each electrode 5. A 4 MHz ceramic resonator controlled oscillator 21 and a CMOS ripple counter frequency divider 22 provide a 125 kHz square wave to generate an alternating electric field in the material. An operational amplifier filter amplifier detector 23 and a logarithmic amplifier 24 pick up the signal from the other electrode 5 and associated contacts 6 and deliver the output to a microcontroller A/D converter 25. This is in turn connected to the main microcontroller described above and indicated in FIG. 3 by the numeral 50.

In more detail, the output from the oscillator 21 is frequency divided by the ripple counter 22 to provide a 125 kHz unity mark space square wave to drive the transmitter electrode 5. The detector 23 filters, amplifies and rectifies the signal from the receiving electrode 5, and drives the logarithmic amplifier circuit 24 which linearises the exponential form of the detected signal and outputs to the A/D converter 25.

The lead 10 is a 6-core cable terminated by a connector which plugs into a socket located at the top end of the housing 2. The meter 1 provides a power supply to the probe 9 and the interface to the probe 9 is via the I$^2$C serial bus cable 10. A link on the probe plug is used to detect when the probe is connected to the instrument. Within the probe 9 a 2.5V stabiliser 30 powers an oscillator 31, in turn driving a pulse width modulator 33. The modulator 33 modulates the output from a relative humidity (RH) capacitive sensor 32 and the modulated signal is routed through an averaging filter 34. A 12-bit A/D converter 35 provides a digital input to a PIC microcontroller 36 mounted within the probe. A temperature sensor IC 40 is also mounted within the probe 9. Both the IC 40 and the microcontroller 36 provide a data signal on the I$^2$C bus 10 for the meter's main microcontroller 50 within the housing 2.

Figure 4C:
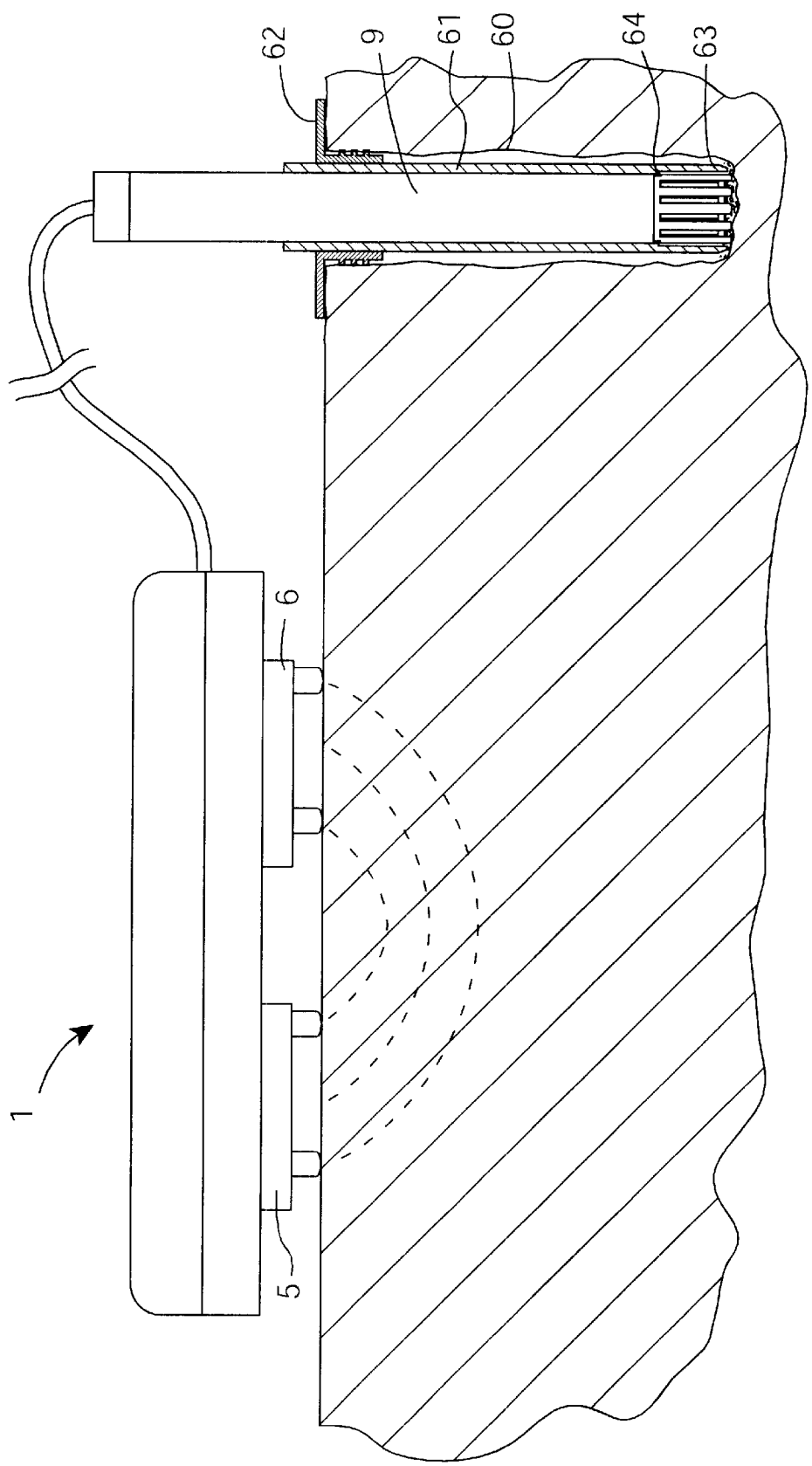
Figure 4D:
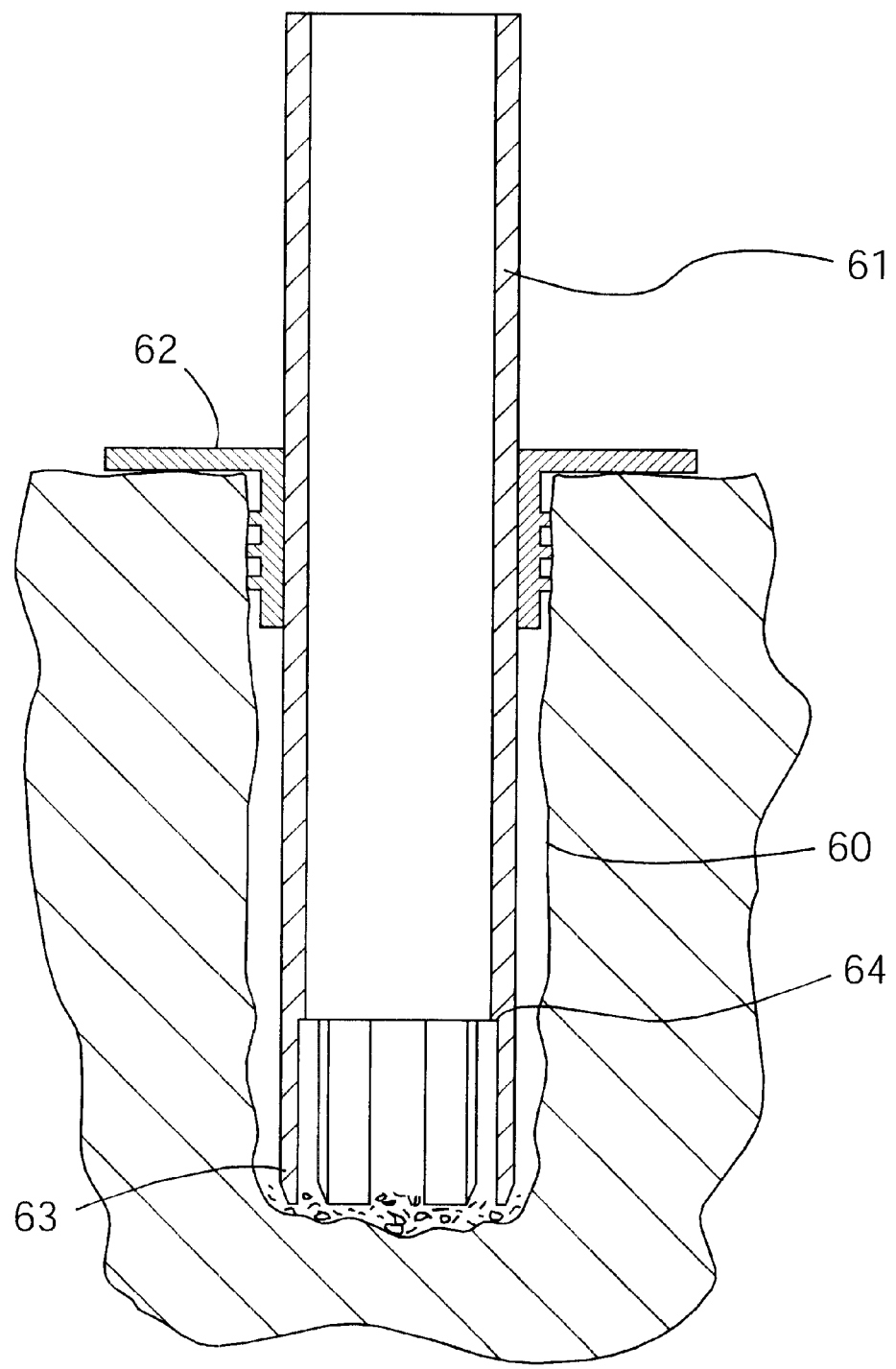

Referring now to FIGS. 4(*a*) to 4(*d*) operation of the meter 1 is described in detail. Moisture content of a concrete slab is to be measured. A bore 60 is drilled in the concrete and a sleeve 61 is inserted into the bore 60. The annular gap around the sleeve 61 at the opening of the bore 60 is sealed by a flexible grommet 62, which also acts to secure the sleeve in place. The inner end of the sleeve 61 is castellated at 63 so that air can enter a sensing space within the sleeve 61. This is illustrated in FIG. 4(*a*), and as shown in FIG. 4(*b*) a rubber bung or plug 65 is inserted into the opening at the outer end of the sleeve 61. This creates a confined sensing space within the sleeve 61, to which access is only allowed at the castellated inner end 63 of the sleeve 61. The plug 65 is left in situ for a period of at least 24 hours so that equilibrium is reached with the relative humidity of the air within the sensing space being representative of the moisture content of the concrete.

As shown in FIG. 4(*c*) the plug is then removed and the probe 9 is inserted with a tight friction-fit between it and the sleeve 61. The inner end of the probe 9 is also castellated so that air within the sensing space penetrates towards the sensing circuitry within the probe body. It will be appreciated from FIG. 4(*c*) that any dust which gathers at the base of the bore does not block air passage because of the castellated shapes of the probe 9 and of the sleeve 61. While the probe 9 is in position within the sleeve 61 the microcontroller 50 processes the signals received from the probe's internal microcontroller 36 and generates a relative humidity reading. At about the same time the user toggles the mode to impedance sensing using the sensor 20 to provide a moisture content reading.

As shown in FIG. 4(*d*), it is not essential that the probe 9 be inserted by its full length. If the bore is shorter the grommet 62 still provides a sealed sensing space and retains the probe 9 in position. This allows excellent versatility because it is sometimes important to obtain readings at different depths to obtain a full "picture" of moisture patterns.

It is possible to have a number of probes within sealed pockets distributed at different places around a building site and to use the meter to plug to each in turn and measure/record the RH/temperature at each location. This is very convenient for the surveyor.

Figure 5:
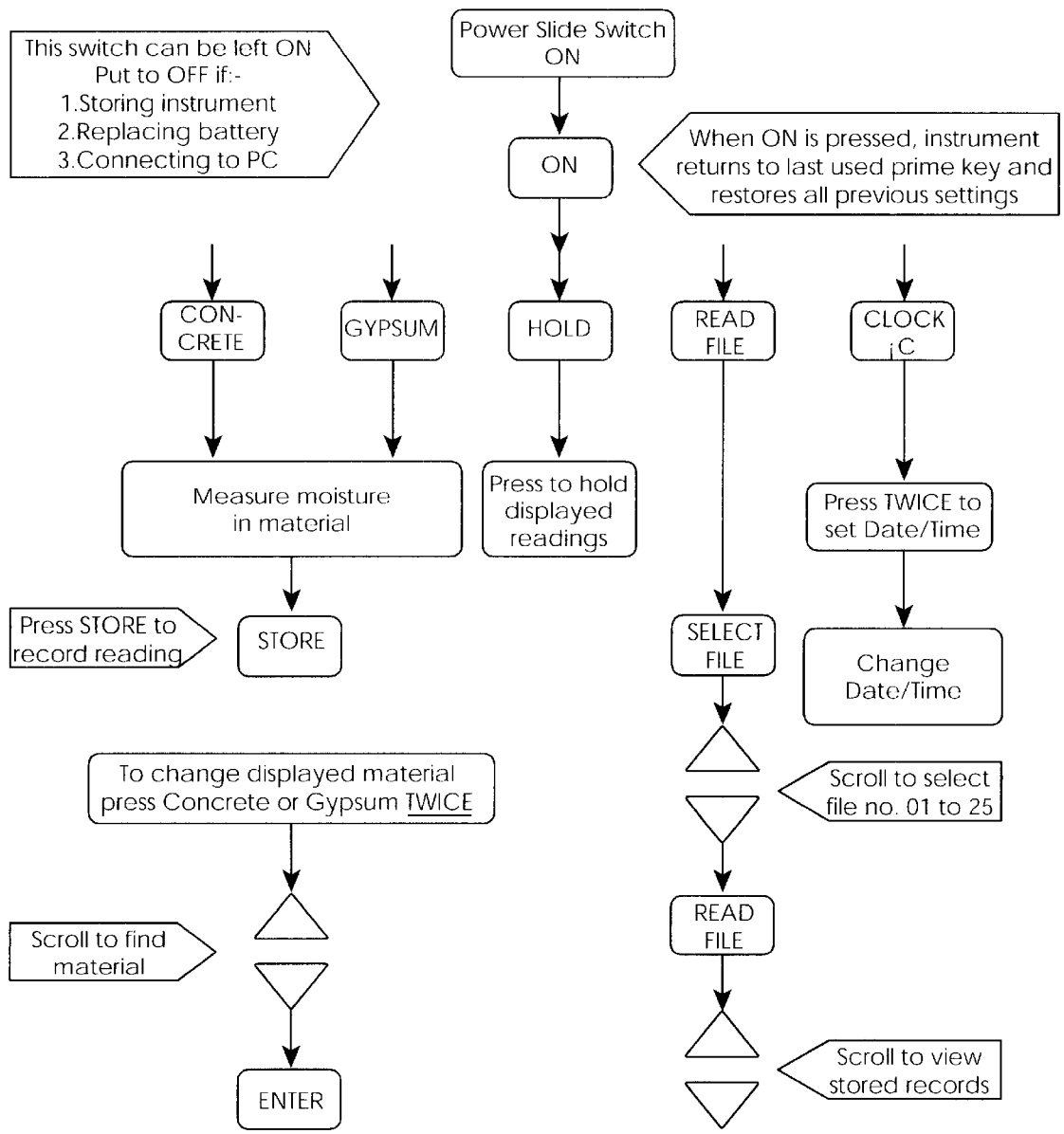
FIG. 5 is a flow diagram illustrating operation of the meter.

The main operating sequence of the meter 1 is shown in FIG. 5. As illustrated, the Hold key is used to hold displayed readings. The Concrete and Gypsum keys are used to select a material type and the Store key is used to store the reading. The readings are taken when the meter 1 is held so that the contacts 6 are in contact with the material, or when the probe 9 is connected to the circuit.

Figure 6:
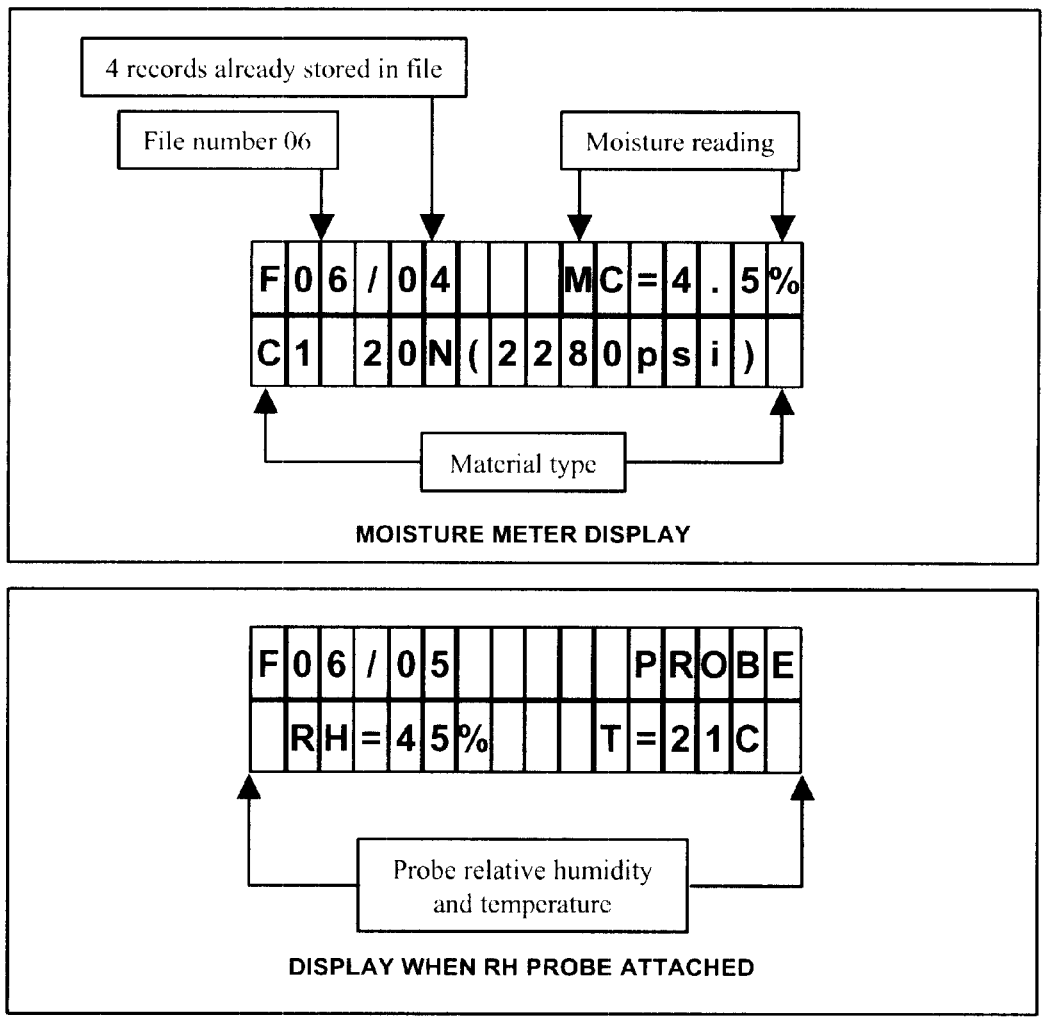
FIGS. 6 to 11 are sample displays illustrating operation of the meter.

As shown in FIG. 6, the meter 1 may provide a moisture content display in which the capacitive/impedance inputs are used to generate a moisture content value, in this case 4.5%. Alternatively, if the probe 9 is used the meter 1 may provide a display of only relative humidity (e.g. 45%) and temperature (e.g. 21° C.). The capacitive/impedance sensing is disabled automatically upon connection of the probe 9.

Figure 7:
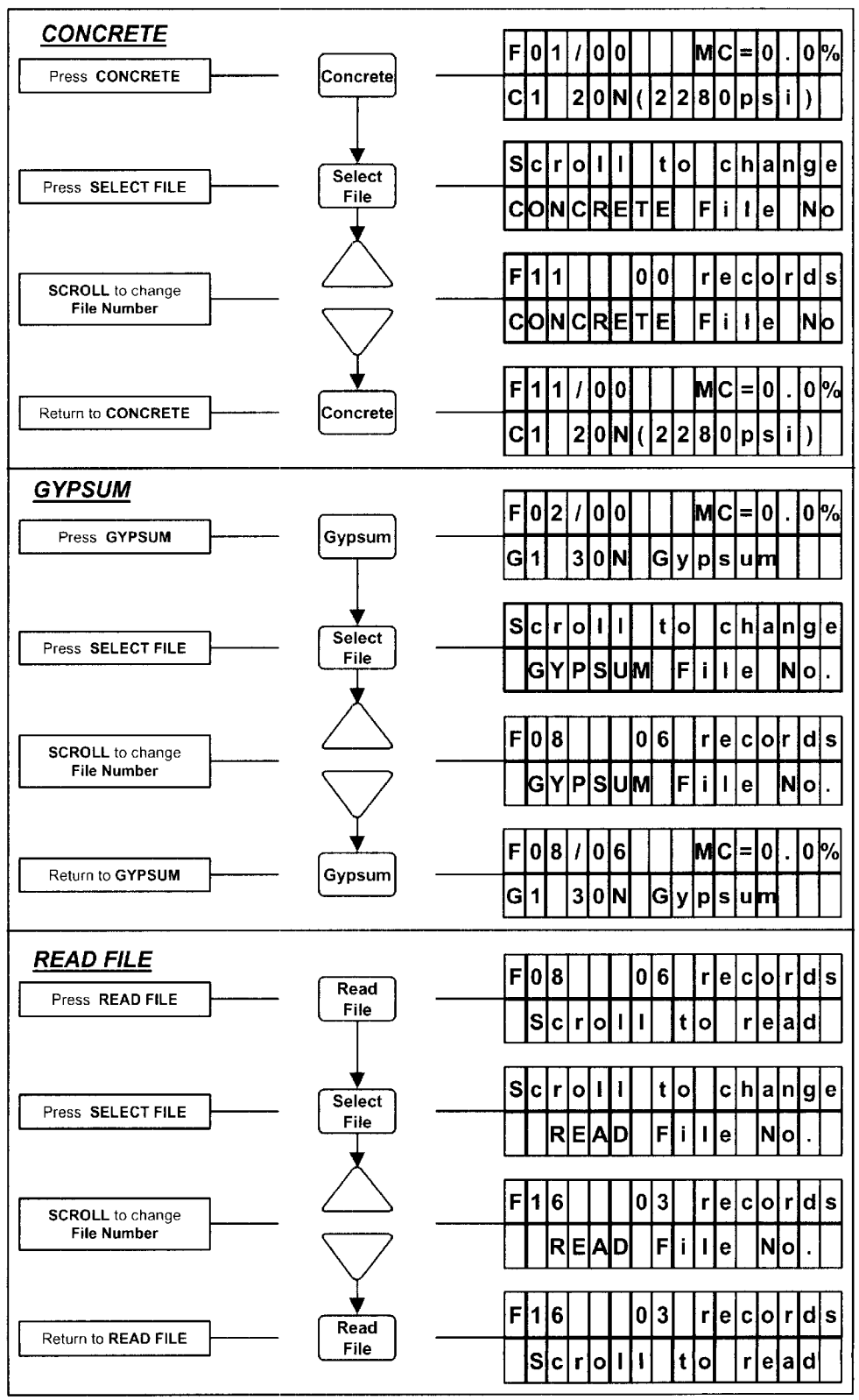
Figure 8:
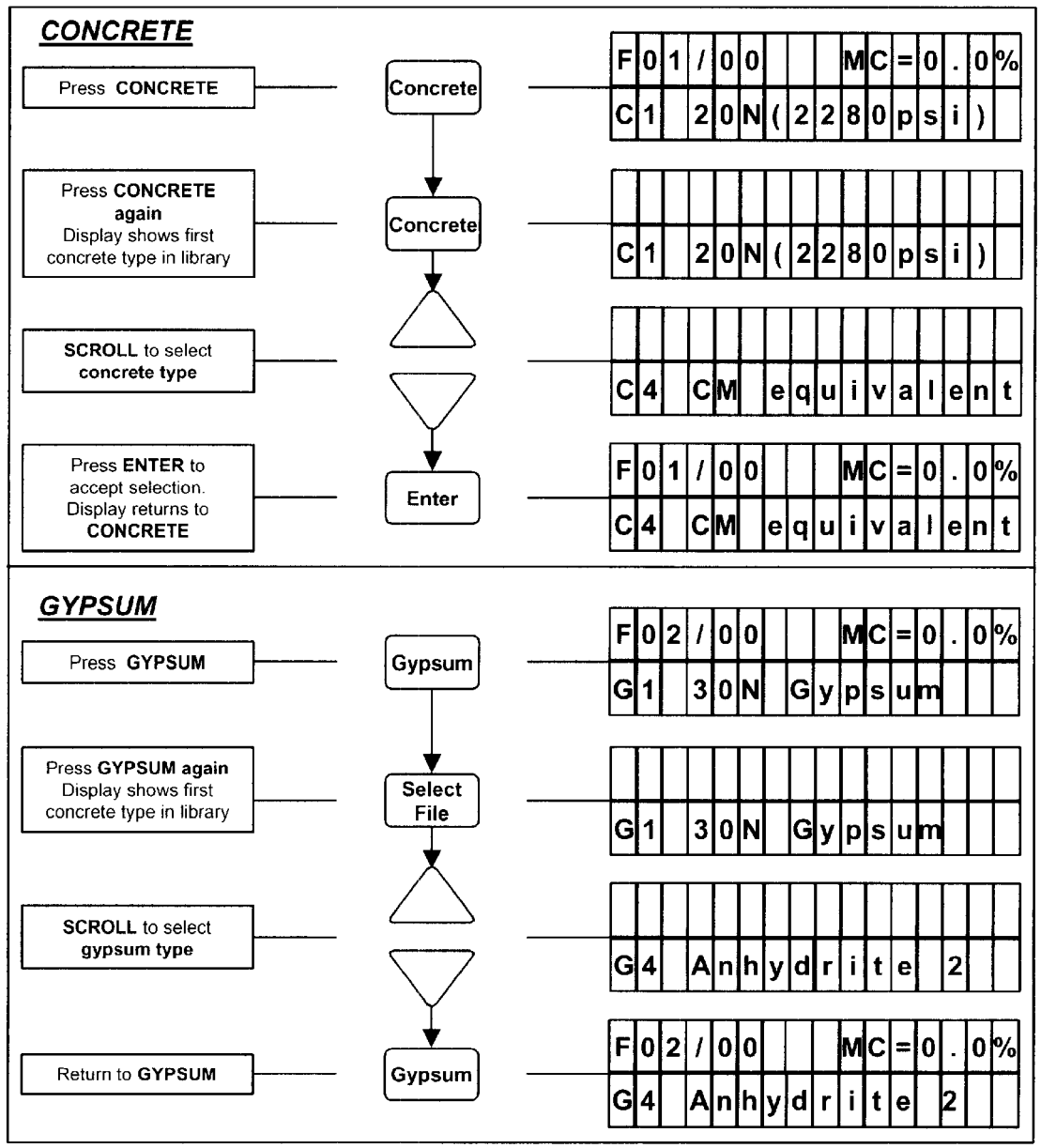
Figure 9:
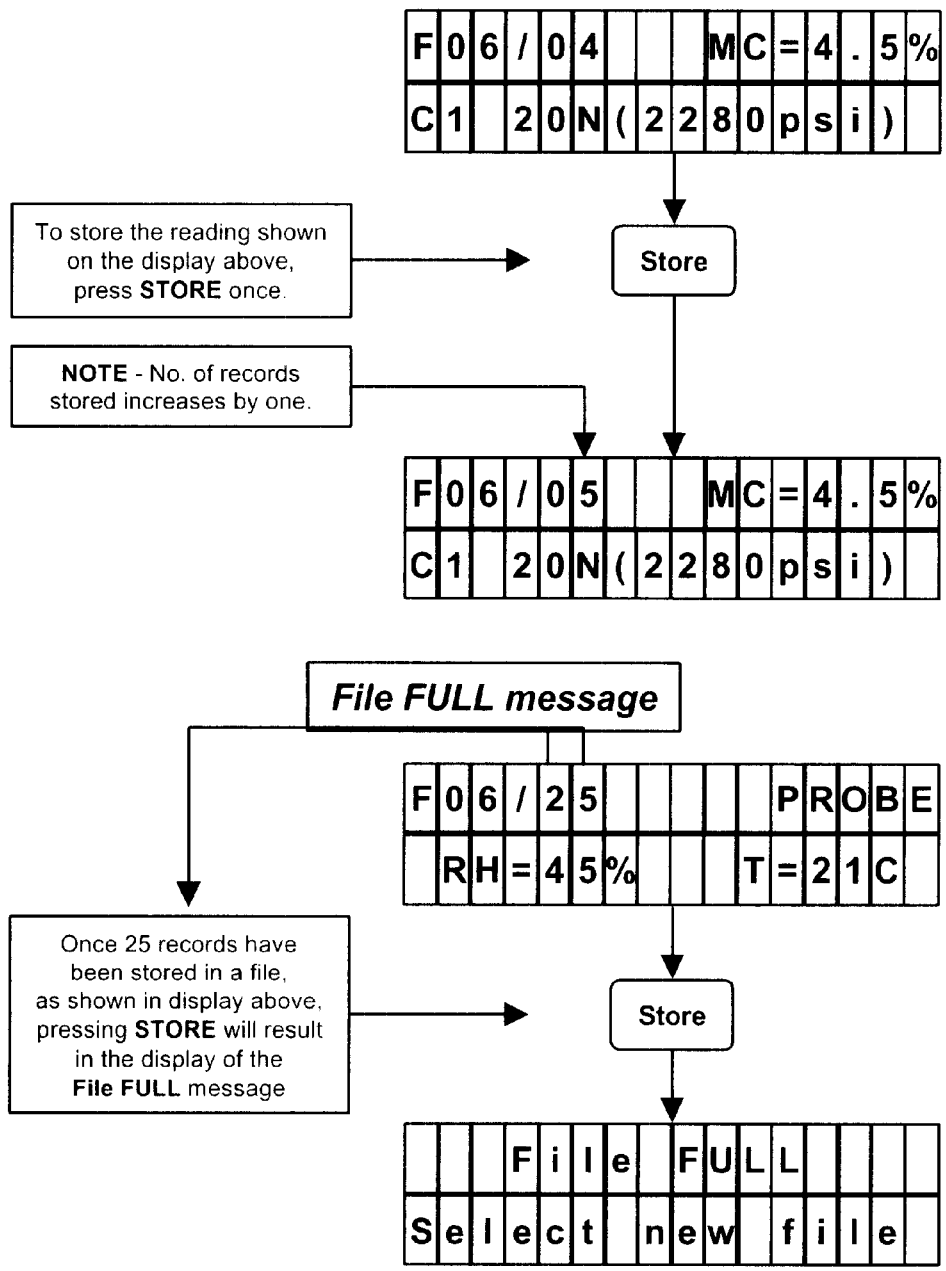
Figure 10:
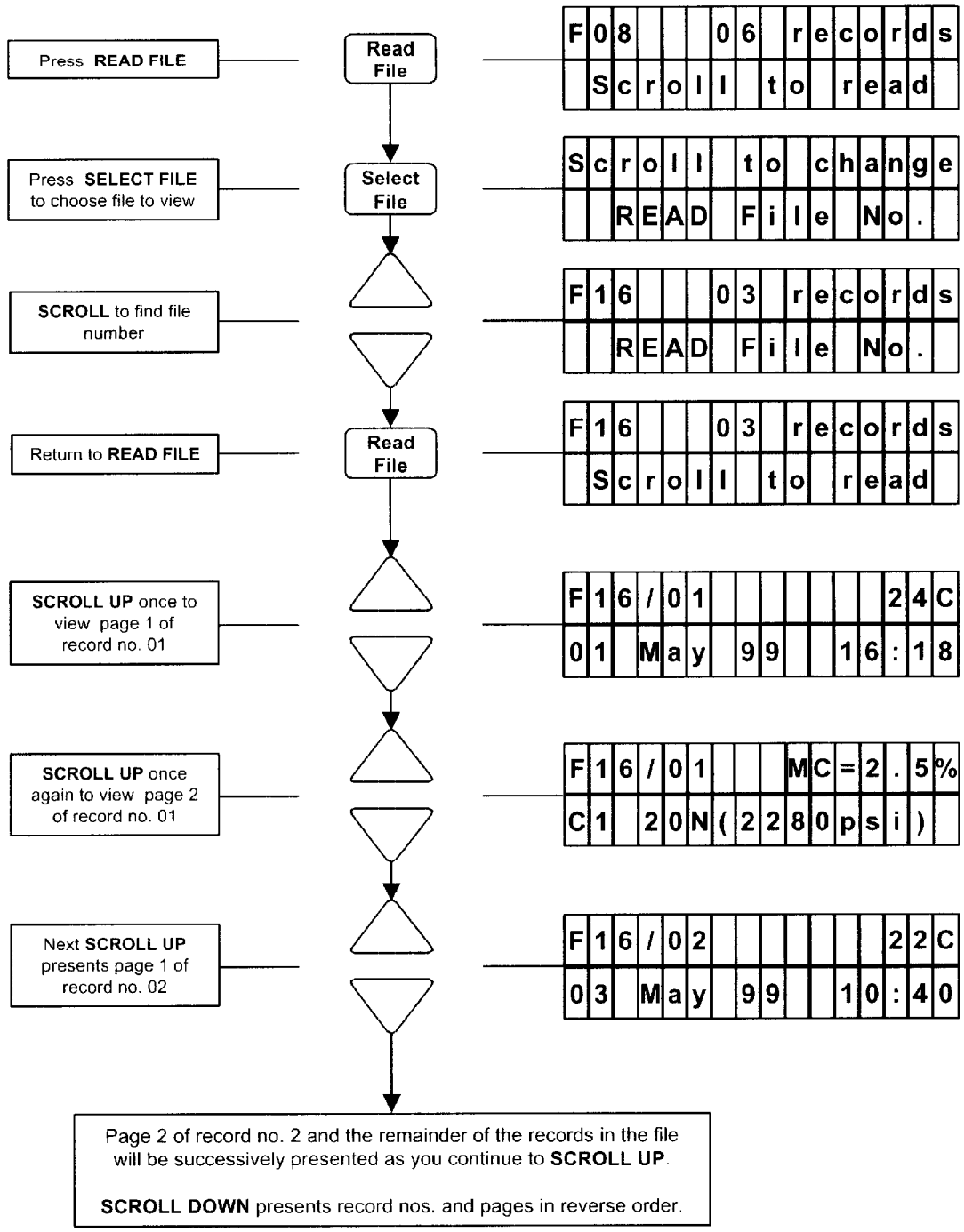
Figure 11:
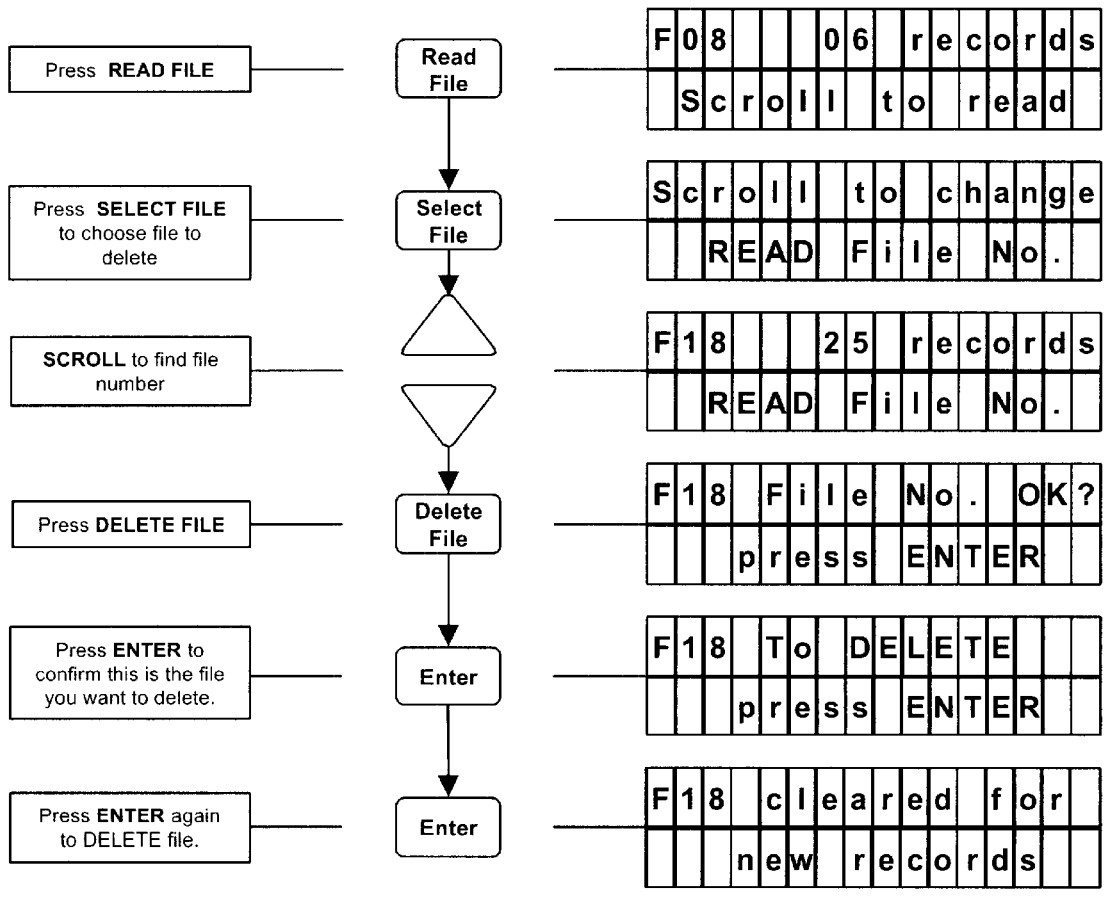

The keypad 3 is used as illustrated in FIG. 7 to select a file, in FIG. 8 to select a material, and in FIG. 9 to store readings. The sequence of FIG. 10 is for viewing stored records, and of FIG. 11 for deleting stored files.

The meter provides a common operating base for each sensor in terms of power supplies, interface electronics, digital processing, LCD display, storage of records, PC interface, PC software facilities and their associated abilities for detailed analysis and graphical presentation of the data. An advantage of the meter 1 is that it provides two independent methods to assess the condition of the material. By reviewing the results from each method, i.e., near surface moisture content as determined by the capactitive sensor and relative humidity/temperature from sealed air pockets located on or in the material, the user is able to make a more accurate appraisal of the condition of the material. This approach provides the following advantages.

Accuracy

The meter can separately measure the near surface moisture content and the internal relative humidity and temperature of concrete or similar material. This means that the moisture content acceptable for local climatic conditions can be rapidly established.

The surveyor has the benefit of two independent readings derived from different types of transducers. In practice, a relationship between measurements is learned by the surveyor with experience, and this increases confidence in the measurements.

Speed

Once the acceptable moisture conditions have been established, capacitive sensor near-surface moisture content readings, which can be taken within a few seconds, will normally suffice to assess the condition of the material for the remainder of the monitoring period.

The invention allows the surveyor to use the relative humidity method to verify the impedance reading to allow for any re-absorption of moisture from ambient air. The meter 1 allows fast moisture readings and simultaneous relative humidity readings which confirm when the concrete has reached the desired moisture conditions such as 75% relative humidity. The invention also overcomes the problems of delay arising from sole reliance on relative humidity measurements because the impedance method can be used for the remainder of the monitoring period after the initial readings.

The invention is not limited to the embodiments described but may be varied in construction and detail.

What is claimed is:

1. A moisture meter comprising:
   a hand-held housing;
   a controller;
   an input interface;
   an output interface;
   an electrical impedance sensor connected to the controller;
   a relative humidity probe connected to the controller; and
   means in the controller for processing signals from the impedance sensor to generate a moisture content output, and for processing signals from the relative humidity probe to generate a relative humidity output.

2. The moisture meter as claimed in claim 1, wherein the controller comprises means for storing material parameter datasets for each of a plurality of materials, means for allowing user selection of a relevant dataset, and means for processing input signals according to the selected dataset.

3. The moisture meter as claimed in claim 2, wherein the controller comprises means for storing a dataset for each of concrete and gypsum.

4. The moisture meter as claimed in claim 3, wherein the controller comprises means for storing a dataset for each of a plurality of concrete and gypsum types.

5. The moisture meter as claimed in claim 1, wherein the relative humidity probe further comprises a temperature sensor and the controller includes means for processing input signals from said sensor and for generating a temperature output.

6. The moisture meter as claimed in claim 1, wherein the impedance sensor includes capacitive electrodes connected to associated drive and pick-up circuits.

7. The moisture meter as claimed in claim 6, wherein each electrode comprises a plurality of spring-loaded contacts for uniform contact with material.

8. The moisture meter as claimed in claim 7, wherein a drive frequency is approximately 125 kHz.

9. The moisture meter as claimed in claim 1, wherein the controller comprises means for storing a data record for each measurement of the impedance sensor and of the relative humidity probe.

10. The moisture meter as claimed in claim 9, wherein the relative humidity probe further comprises a temperature sensor and the controller includes means for writing temperature data to a relative humidity data record.

11. The moisture meter as claimed in claim 1, wherein the relative humidity probe comprises a capacitive sensor, a pulse width modulator for modulating output of the capacitive sensor and an averaging filter for averaging the modulated signal.

12. The moisture meter as claimed in claim 11, wherein the probe further comprises a digital microcontroller connected to receive an output from the averaging filter via an analog to digital converter.

13. The moisture meter as claimed in claim 1, wherein the probe comprises a housing of tubular shape including openings at an inner end for access by air to internal sensing components.

14. The moisture meter as claimed in claim 13, wherein the probe housing is of castellated shape at its inner end.

15. The moisture meter is claimed in claim 13, wherein the probe further comprises a grommet including means for sealing around the probe at the mouth of a bore.

16. The moisture meter as claimed in claim 13, wherein the probe further comprises a sleeve including means for receiving the probe body when inserted in a bore.

17. The moisture meter as claimed in claim 16, further comprising a grommet including means for sealing around the probe at a mouth of a bore, wherein the sleeve is a friction fit within the grommet.

* * * * *